United States Patent [19]

DeNiro

[11] Patent Number: 4,913,176

[45] Date of Patent: Apr. 3, 1990

[54] DENTAL PICK

[76] Inventor: Richard G. DeNiro, 1118 E. Adams, Orange, Calif. 92667

[21] Appl. No.: 243,449

[22] Filed: Sep. 12, 1988

[51] Int. Cl.$^4$ .............................................. A61C 15/00
[52] U.S. Cl. .................................... 132/329; 433/80; 433/141
[58] Field of Search ........................ 132/321, 322, 329; 433/80, 141, 143; 128/62 A

[56] References Cited

U.S. PATENT DOCUMENTS

| | | | |
|---|---|---|---|
| 774,253 | 11/1904 | Keefe | 132/329 |
| 1,674,547 | 6/1928 | Hayden | 433/141 |
| 1,784,986 | 12/1930 | Eisenberg | 132/329 |
| 2,016,597 | 10/1935 | Drake | 128/62 A |
| 2,552,134 | 5/1951 | Berliner | 423/143 |
| 2,677,843 | 5/1954 | Goodman | 433/143 |
| 2,762,501 | 9/1956 | Cameron | 132/329 |
| 3,438,486 | 4/1969 | Pinkas | 132/321 |
| 3,605,765 | 9/1971 | Canby | 132/329 |
| 3,771,537 | 11/1973 | Schole | 433/142 |
| 3,809,103 | 5/1974 | Bender | 132/329 |
| 4,314,574 | 2/1982 | Inerte | 132/329 |
| 4,449,934 | 5/1984 | Salam | 433/143 |
| 4,505,678 | 3/1985 | Andersson | 433/143 |
| 4,616,667 | 10/1986 | Tang | 132/329 |
| 4,643,676 | 2/1987 | Jansheski | 433/143 |

FOREIGN PATENT DOCUMENTS

| | | | |
|---|---|---|---|
| 511967 | 4/1929 | Fed. Rep. of Germany | 433/141 |
| 211202 | 11/1940 | Switzerland | 132/329 |
| 2059266 | 4/1981 | United Kingdom | 132/329 |

OTHER PUBLICATIONS

Pader, Morton, *Oral Hygiene Products and Practice*, Marcel Dekker, Inc., 1988, pp. 179–192.

*Primary Examiner*—John J. Wilson
*Attorney, Agent, or Firm*—Knobbe, Martens, Olson & Bear

[57] ABSTRACT

A dental pick having an enlarged head for removing plaque between teeth is disclosed. The pick has a handle portion and an operational portion. The handle portion has two gripping portions to provide two different operational lengths for the pick. The operational portion includes a flexible neck portion and an enlarged head portion. Advantageously, the operational portion of the pick is of a substantially continuous, non-tapering thickness which enables the pick to be inserted into the interproximal spaces between adjacent teeth without the risk of becoming impacted. The pick is adapted to slide between adjacent teeth while in a vertical orientation, and is then rotated so that the larger vertical portion of the head assumes a generally horizontal orientation. Once the device is substantially horizontally oriented, the pick is agitated both vertically and horizontally so as to disrupt food, plaque and bacteria residing therein.

3 Claims, 2 Drawing Sheets

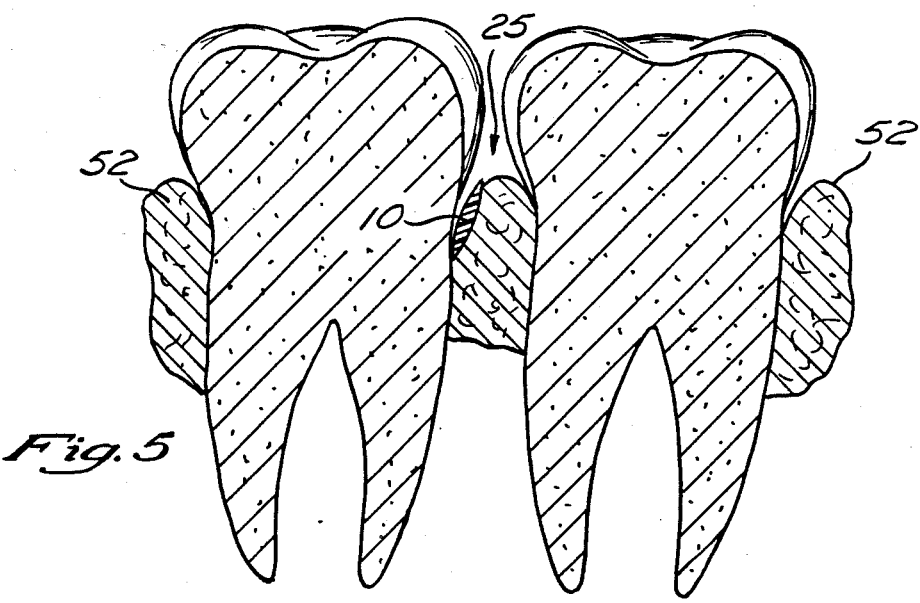
Fig. 5
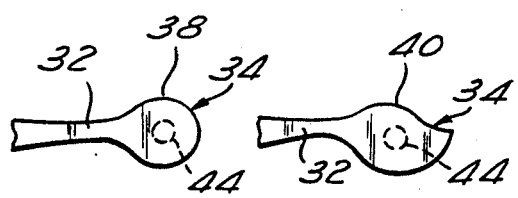
Fig. 6
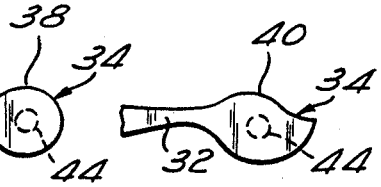
Fig. 7
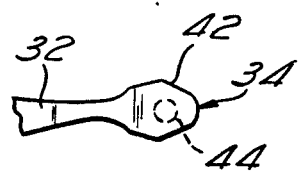
Fig. 8
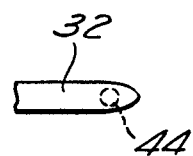
Fig. 9
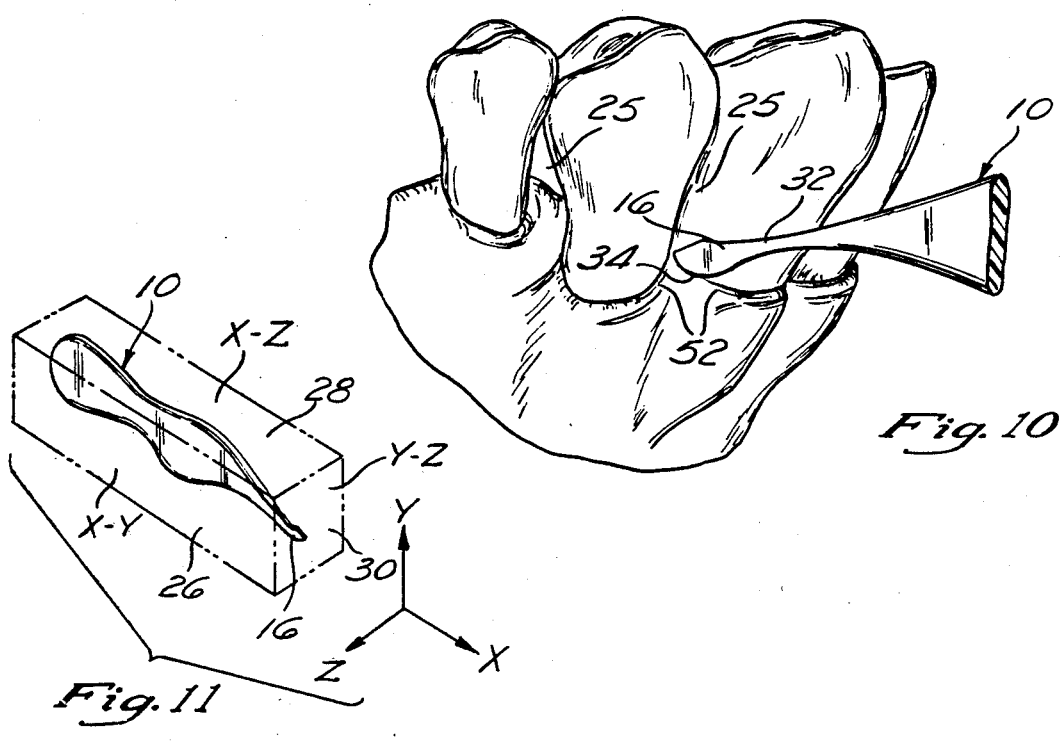
Fig. 10
Fig. 11

DENTAL PICK

BACKGROUND OF THE INVENTION

The present invention relates generally to the field of dental instruments. More specifically, the present invention relates to a dental pick for removing food and plaque deposits from areas of the teeth and gums that are not accessible with a toothbrush.

It is well known that proper oral hygiene requires a frequent and regular regimen of teeth cleaning in order to remove food particles and plaque from the teeth. The toothbrush is the most commonly used instrument for cleaning the teeth, however there are certain areas of the teeth that the toothbrush cannot properly clean. These areas include the interproximal spaces between adjacent teeth as well as the surfaces of the teeth close to and beneath the gum line.

The interproximal space between adjacent teeth is somewhat triangular and normally filled with gingival tissue, and specifically is referred to as the gingival papilla. The gingiva, or gum, is the soft tissue in the mouth which covers the alveolar bone and surrounds the teeth. Proper contact and alignment of adjoining teeth allow proper spacing between the teeth for the necessary gingival tissue which is attached to the alveolar bone and the teeth for protection. A shallow pocket, or sulcus is formed close to the gum line, at the junction of the gum and tooth.

In general, most teeth do not have a uniform round shape. More specifically, indentations or depressions are commonly found on the surfaces of the teeth, and are generally referred to as developmental depressions. Due to the irregular surfaces of the teeth, there exist certain areas which cannot be thoroughly cleaned using currently available dental devices. In particular, the developmental depressions formed on the opposing vertical faces of adjacent teeth are especially difficult to clean, even by dental professionals.

Heretofore, outside of a dentist's office, dental floss has primarily been used by the patient to remove plaque from between the teeth. When used properly, dental floss removes plaque accumulating in the gaps between the teeth by a shaving or scaling action with the floss being slid back and forth between the interproximal spaces of the teeth. In most instances, the shape of the tooth is such that when dental floss is used, it rides on the corners of the teeth and thus does not enter the developmental depressions. Moreover, a tight contact between adjacent teeth makes it difficult to slide the floss between the teeth. In such cases, while it is possible to force the floss therebetween, the rebound caused by the force used to pass the floss between the teeth can traumatize the tender gingival tissue. Further, dental floss cannot be used to clean the gum line pockets on the lingual or facial sides of the teeth.

In addition to dental floss, there have been a number of rigid toothpick type devices used for the cleaning and scraping of the teeth. U.S. Pat. No. 2,016,597, for example, describes a device for tooth cleaning and gum stimulating which is triangular in cross section and has a tapered form. The tapered form of this device enables it to enter the interproximal spaces, and the triangular cross-sectional shape allows the flat sides of the device to engage the surfaces of the tooth. This device, however, can become impacted between tightly adjoining teeth due to the tapered, triangular design and further, this device is too bulky to allow subgingival cleaning.

Another tooth cleaning implement is described in Schole U.S. Pat. No. 3,771,537. The Schole reference teaches the use of a thin pick to clean plaque deposits from between teeth. While the risk of becoming impacted is substantially eliminated, the flat, blunt end of the device makes it unsuitable for cleaning below the gum line, an area in which a large percentage of plaque and bacteria accumulate.

As plaque accumulates in the areas where prior devices are unable to clean, the gums become increasingly irritated and the pockets between the teeth and gums deepen, resulting in the accumulation of even more plaque and the formation of a bacteriological environment. The result of such accumulation of bacteria is gingivitis, a disease which affects the gum tissue, or gingiva. If, however, the degenerative process extends into the deeper structures, it is known as periodontal disease. Periodontal disease is an inflammatory lesion caused by bacteria affecting the tissues housing the roots of the teeth. This disease, sometimes referred to as pyorrhea, increases in prevalence and severity with increasing age. In general, the diseased tissue appears abnormally red and slightly swollen. Further, the diseased gingiva tends to bleed, sometimes profusely, when the teeth are brushed. In some cases, the gums may become thickened and scarred, and may recede, exposing the root surface. As the disease advances, the attachment of the gum to the tooth is lost and the alveolar bone is resorbed, causing the teeth to become loose, eventually to the point where they fall out.

Both gingivitis and periodontal disease are caused by microorganisms which form plaque on the surfaces of the teeth at the gingival pocket or sulcus, as well as within the developmental depressions. As the plaque calcifies, it becomes calculus or tartar. Tartar tends to be hard, and brushes and dental floss are not suited to removing it. Rather, tartar needs to be chiselled off the teeth.

As with most diseases, prevention is the key to success. Unfortunately, use of the above devices have a number of significant drawbacks. First of all, dental floss requires the use of two hands for proper agitation of food particles and provides the best results when done in front of a mirror. This severely limits the usage of floss during otherwise idle time such as television watching or commuting. Due to the shortcomings of the aforementioned devices, many have turned to chemical means to destroy the bacteria within the mouth. This too leads to undesirable consequences, as some of the bacteria in the mouth are vitally important, and are indiscriminately destroyed by such chemicals.

Accordingly, there is a need in the art for a simple to use device, which encourages thorough teeth cleaning on a daily basis in conjunction with regular brushing to prevent plaque from accumulating in the interproximal spaces between the teeth, as well as in the developmental depressions and gum line pockets, so as to thwart the formation of tartar.

SUMMARY OF THE INVENTION

Briefly, the present invention is a dental pick having a handle portion for grasping the device and an operative portion for between teeth cleaning. Advantageously, the dental pick of the present invention has a thickness selected such that the operative end of the pick will be thin enough to be easily inserted between adjacent teeth, yet thick enough to provide the device with enough structural rigidity to remove plaque and disrupt bacteria. Significantly, the operational end of the pick is quite narrow, and may be easily inserted between adjacent teeth as well as subgingivally. Further, the thinness of the operational portion of the pick makes it flexible so as to facilitate angulation of the device. Unlike prior devices, when the pick is used to remove plaque and disrupt bacteria subgingivally, it relies on the resilience of the gingival papilla to bias the operational end of the pick to engage the tooth, rather than its own structural rigidity.

Preferably, the handle portion has an hourglass-like shape, and is of a thickness greater than that of the operational portion, so as to provide structural support for the pick. The hourglass design of the handle portion provides two convenient areas for placing one's forefinger to manipulate the pick, thus providing two operational lengths. Advantageously, the handle portion narrows more abruptly on the underside as it stems toward the operational end so as to provide added structural support for that portion of the handle on which the user's forefinger presses.

In one embodiment, the operational portion includes a head disposed at the distal end thereof. One preferred head configuration has an elongated diamond shape with a curved lower edge and an upper edge having angular vertices. In addition, several alternative head configurations are also disclosed. The head portion is useful in cleaning the outer shoulders and inner corners of between adjacent teeth, as well as stirring up bacteria within the developmental depression areas. It is noteworthy that the operational end of the device, with or without the head, is both thin enough and long enough to extend through the interproximal spaces from the facial side all the way through to the lingual side of the teeth.

In a further alternative embodiment, a depression or, alternatively, a hole is provided in the head of the device for receiving and retaining medicaments for later dispensation at selected sites. This enables one to selectively rid certain areas of the mouth of undesirable bacteria which were heretofore inaccessible, even with rinses.

There are several ways in which the dental pick of the present invention can be utilized for thorough cleaning of the teeth. In one mode of operation, the pick is oriented vertically and inserted between two adjacent teeth. Once disposed between the teeth, the dental pick can be rotated so that the larger portion of the head assumes a generally horizontal position. The pick is then be moved vertically and horizontally to provide an agitating action against the less accessible areas of the teeth to disrupt any bacteria forming therein. This method is particularly useful for disrupting bacteria in the developmental depressions and for removing plaque from the outer shoulders and inner corners of the teeth.

The dental pick of the present invention is also adapted to disrupt bacteria below the gum line. When used for this purpose, the operational portion is inserted subgingivally and utilizes the resiliency of the gingival papilla to bias the pick towards the tooth. Thus, the structural rigidity lost by the thinness of the operational portion does not adversely affect the toot cleaning function.

Further objects, features and other advantages of the present invention will become apparent from the ensuing detailed description, considered together with the appended drawings.

BRIEF DESCRIPTION OF THE DRAWINGS

FIG. 5 is a cross-sectional view of the dental pick of the present invention being forced against the tooth by the gingival papilla so as to bias the pick toward the developmental depressions existing therebetween;

FIG. 6 is a plan view of an alternative embodiment of the head portion of the pick;

FIG. 7 is a plan view of a second alternative embodiment of the head portion of the pick;

FIG. 8 is a plan view of a third alternative embodiment of the head portion of the pick;

FIG. 9 is a plan view of a fourth alternative embodiment of the head portion of the pick;

FIG. 10 is an enlarged perspective view of the facial side of the bottom teeth, with the dental pick of the present invention readied for insertion therebetween; and FIG. 11 is an isometric view of the dental pick of the present invention, illustrating the three different planes in which the pick lies.

DETAILED DESCRIPTION OF THE PREFERRED EMBODIMENT

Figure 1:
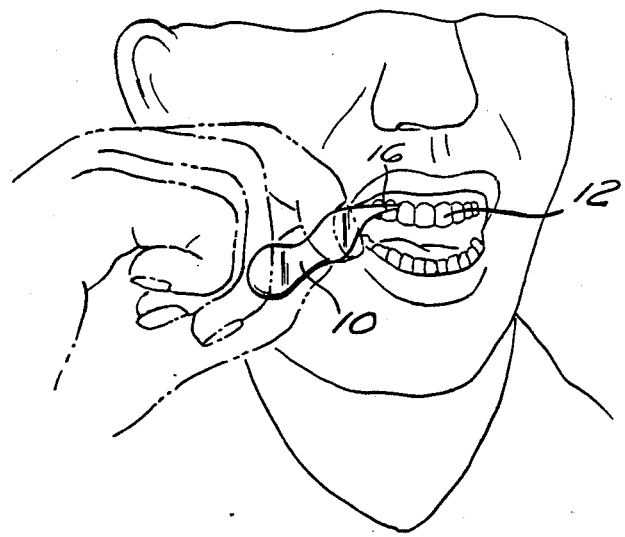
FIG. 1 illustrates a preferred form of a dental pick of the present invention as being used by a person to clean his front teeth.
Figure 2:
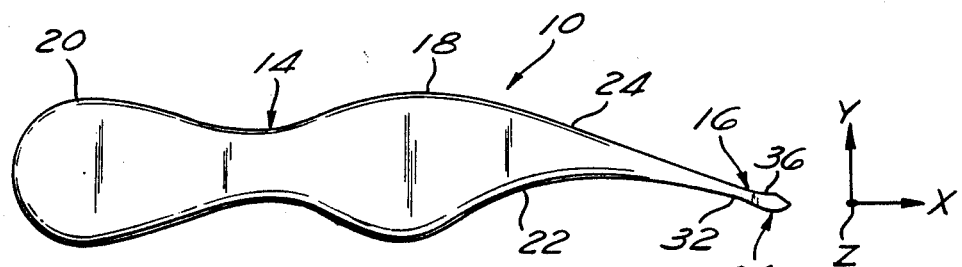
FIG. 2 is a plan view of the dental pick of the present invention.

Referring now to the drawings in detail, wherein like reference numerals designate like elements throughout the several views thereof, in FIG. 1, there is shown generally at 10, a dental pick embodying the present invention in a preferred form, as being used by a person to clean his front teeth 12. As more clearly illustrated by FIG. 2, the dental pick 10 of the present invention has an hourglass shaped handle portion 14 and an elongate operational portion 16. The handle portion 14 includes distal and proximal enlarged gripping portions 18, 20, respectively, corresponding to the enlarged bulbous portions of the hourglass shape.

The dental pick 10 of the present invention is preferably constructed of a flexible material, such as polypropylene. Preferably, the distal gripping portion 18 is at least 0.5" wide or wider at its widest point, and approximately 1.5" in length. The proximal gripping portion 20 need not be as wide nor as long as the distal gripping portion 18, and is preferably along the order of 0.45" in width and approximately 0.7" in length. The distal gripping portion 18 begins to taper and narrow as it approaches the operational end 16 of the pick 10. It is noteworthy that the majority of the narrowing takes place on the underside, or bottom portion 22 of the pick 10. Thus, as the handle portion 14 of the pick approaches the operational portion 16 thereof, only a gradual downward curvature exists on the upper portion 24 while a more pronounced and well defined upward curvature exists on the bottom portion 22. This is significant in that it provides the upper portion 24 of the pick with rigidity and strength so as to facilitate use and manipulation of the pick 10 by placing one's forefinger on the upper portion 24.

If, for example, it is desirable to clean the front teeth, such as the incisors or canines, the distal gripping portion 18 is held, with the forefinger pushing downwardly on the upper portion 24 adjacent the operational end. If, however, it is desirable to clean the back teeth, such as the molars and premolars, the proximal gripping portion 20 should be grasped. Thus, the handle 14 has two operational lengths. For further support and durability, the handle portion 14 is substantially thicker than the operational end 16 of the pick. It has been determined that a thickness of at least 0.075" is sufficient to provide the necessary structural support for the pick.

Disposed at the distal end of the handle portion 14, and integrally connected thereto is the operational portion 16. Advantageously, the operational portion 16 of the pick 10 is relatively thin and flexible, so as to facilitate passage between the teeth and preferably exhibits a thickness of 0.025" or less. This is significant in that it allows the user of the pick 10 to easily insert and position the operational portion between the teeth and subgingivally. The pick then utilizes the resiliency of the gingiva 52 but to force the operational end towards the tooth so as to disrupt any bacteria developing therebetween. As shown in cross-section in FIG. 5, the gingival papilla 52 biases the pick toward the tooth, and movement of the pick within the interproximal area 25 effects cleaning thereof.

Figure 3:
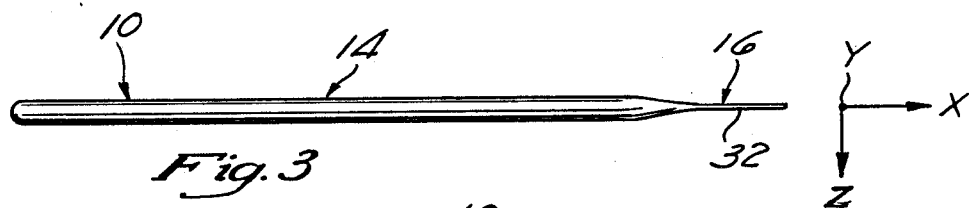
FIG. 3 is a side view of the dental pick, illustrating the uniformity of the neck thickness.

As illustrated in FIG. 11 by the three dimensional box in phantom lines, the dental pick 10 of the present invention can be thought of as lying in three elevational planes. The X-Y or vertical longitudinal elevational plane 26 corresponds to the view depicted in FIG. 2. The X-Z, or horizontal longitudinal elevational plane 28 corresponds to the view depicted in FIG. 3. Both the X-Y and X-Z planes 26, 28 are considered longitudinal planes since they extend parallel to a longitudinal axis (not shown) of the pick 10. The Y-Z, or transverse plane 30 would show an end view of the dental instrument 10 of the present invention. Significantly, as depicted in FIG. 3, the operational end 16 of the pick 10 is of a substantially Constant thickness in one plane, preferably the horizontal longitudinal plane, or the X-Z plane 28. Most preferably, to allow for easy insertion, the pick 10 is oriented so that the horizontal longitudinal plane 28 is transverse to the interproximal spaces 25 between the teeth.

This feature of maintaining a constant thickness at the operational portion 16 of the dental pick 10 is significant in that it allows the operational end 16 to be inserted between the teeth from the facial side all the way through to the lingual side without the risk of becoming impacted between the teeth. Further, the structural rigidity lost by the thinness of the operational portion 16 does not adversely affect the tooth cleaning functions of the pick 10. This is because the pick is flexible enough to be forced against the teeth by the gingival papilla 52.

Preferably, the operational portion 16 is at least 0.375" in length so as to enable passage all the way through the teeth and includes a flexible neck portion 32, and a head portion 34. Preferably, the neck portion 32 of the pick 10 has a length of approximately 0.250" and can be easily bent to assist in varying the angle of the head portion 34 of the device without the fear of breakage. Thus, the user of the pick is able to bend the operational end of the pick to a desired angle so as to facilitate insertion between some of the more difficult to reach areas of the teeth. Significantly, at least a segment of the neck portion 32 of the pick 10 is sufficiently narrow to enable that portion of the pick to be positioned entirely subgingivally.

The head 34 of the pick 10 is approximately 0.125" in length, and in one embodiment, exhibits an elongated diamond shape 36 with a curved lower edge and an upper edge having angular vertices. The diamond-like shape of the head 36 aids in stirring up the food, plaque and other bacteria trapped within the developmental depressions 50 between the teeth.

In an alternative embodiments, as illustrated in FIGS. 6–9, the head portion 34 of the pick 10 can take on any number of shapes. FIG. 6, for example, illustrates an elongate neck 32 with a rounded bulbous head 38, while FIG. 7 shows a head portion 40 having a sinusoidal upper edge and a rounded lower edge, and FIG. 8 a partially rounded, substantially hexagonal head portion 42. In some instances, it may be desirable not to have a head portion at all, but rather, a continuous elongate neck portion, as is illustrated in FIG. 9.

Additionally, as shown in each of FIGS. 6–9 in broken lines, the distal tip of the operational end 16 may be equipped with a means for retaining a medicament 44 for controlled dispensation within the mouth at preselected areas. For example, an anti-bacterial solution sold under the name Peridex may be used in combination with the present pick for use in selected areas. Preferably, this means for retaining a medicament is in the form of a depression on one side of the device. Alternatively, however, the means for retaining may comprise a hole passing all the way through the distal tip of the device, or other equivalent structures. In either case, the medicament retaining means enables one to kill off undesirable bacteria accumulating in certain selected areas of the mouth without disturbing the naturally occurring and much needed bacteria throughout the remainder of the mouth.

Figure 4:
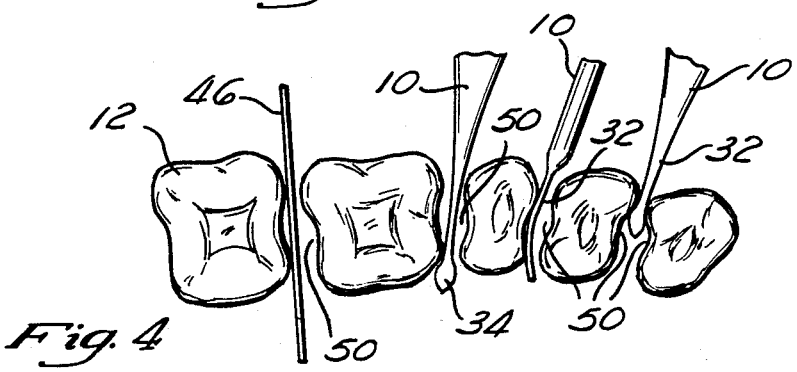
FIG. 4 is a plan view, illustrating the inability of floss to reach into the developmental depressions and the use of the dental pick of the present invention.

The present pick 10 is particularly suited to cleaning the developmental depressions 50 found between adjacent molars and premolars. As illustrated in FIG. 4, prior art cleaning devices, such as dental floss 46 rides on the outer shoulders of the teeth, and does not penetrate into the developmental depression regions 50. The dental pick 10 of the present invention overcomes this deficiency by bending into place under the force of the gingival papilla. Also, any one of the head portions illustrated in FIGS. 2, 6, 7 or 8 are effective in reaching into the developmental depressions 50 for thorough cleaning in these seldom cleaned areas. Further, the head portion 34 improves the cleaning of the edges of the teeth, particularly around the inner corners and outer shoulders thereof, as shown in FIG. 4.

In operation, the pick 10 is oriented vertically, as shown in FIG. 10 for initial insertion into the interproximal areas 25 between the teeth. The continuous width of the pick 10 at the operational end 16 enables the pick 10 to slide through the interproximal space 25 from the facial side to the lingual side without becoming impacted therein. Further, since the pick 10 is adapted to slide between the teeth at the interproximal area 25, the risk of traumatizing the gingival papilla 52 as with dental floss 46 is substantially eliminated.

Once the operational portion 16 is vertically inserted between adjacent teeth, and the head 34 is proximate to the developmental depression 50, the pick 10 is rotated so that the larger vertical portion of the head 34 assumes a generally horizontal orientation. With the pick 10 horizontally oriented between the teeth, it can then be agitated both vertically and horizontally to disrupt the bacteria residing therebetween. The pick 10 can also be used in a manner akin to dental floss 46, as the operational portion 16 is allowed to pass through the space between adjacent teeth from the facial side to the lingual side and vice versa.

Although only the preferred forms of the invention have been illustrated and exemplified, it will be apparent to those skilled in the art that various modifications may be made therein without departing from the spirit of the invention or from the scope of the appended claims.

What is claimed is:

1. A dental instrument for removing food, plaque, and other debris from the interproximal spaces between teeth and subgingivally, said instrument comprising:
   a handle portion for gripping and providing structural support to the device, said handle portion being hourglass shaped and including first and second enlarged bulbous gripping portions, for enabling the device to be grasped and used at two different operational lengths; and
   an elongated neck portion, having a proximal end and a distal end and integrally connected to said handle portion, said neck portion adapted for insertion between adjacent teeth, said neck portion having a thickness substantially less than the thickness of said handle portion, said thickness of said neck portion also having a substantially constant thickness in at least one longitudinal elevational plane, wherein at least a segment of said neck portion is sufficiently narrow to enable said segment to be positioned entirely subgingivally.

2. A dental instrument as defined by claim 1, wherein said one of said enlarged gripping portions is longer than the other.

3. A dental instrument for removing food, plaque, and other debris from the interproximal spaces between teeth and subgingivally, said instrument comprising:
   a handle portion for gripping and providing structural support to the device;
   an elongated neck portion, having a proximal end and a distal end and integrally connected to said handle portion, said neck portion adapted for insertion between adjacent teeth, said neck portion having a thickness substantially less than the thickness of said handle portion, said thickness of said neck portion also having a substantially constant thickness in at least one longitudinal elevational plane, wherein at least a segment of said neck portion is sufficiently narrow to enable said segment to be positioned entirely subgingivally; and
   means for retaining a medicament for selective placement within the mouth, said means defining a hole through said elongated neck portion and proximate said distal end thereof, said hole having a diameter sufficiently small so that the surface tension of said medicament retains said medicament in said hole.

* * * * *